US009050271B2

(12) United States Patent
Kobayashi et al.

(10) Patent No.: US 9,050,271 B2
(45) **Date of Patent: *Jun. 9, 2015**

(54) ANTIMYCOTIC PHARMACEUTICAL COMPOSITION

(75) Inventors: Hirokazu Kobayashi, Yokohama (JP); Eiko Kosugi, Yokohama (JP); Nobuo Kubota, Yokohama (JP)

(73) Assignees: POLA PHARMA INC., Tokyo (JP); NIHON NOHYAKU CO., LTD., Tokyo (JP)

( * ) Notice: Subject to any disclaimer, the term of this patent is extended or adjusted under 35 U.S.C. 154(b) by 403 days.

This patent is subject to a terminal disclaimer.

(21) Appl. No.: 13/258,324

(22) PCT Filed: Apr. 9, 2010

(86) PCT No.: PCT/JP2010/056884

§ 371 (c)(1), (2), (4) Date: Sep. 21, 2011

(87) PCT Pub. No.: WO2010/117091

PCT Pub. Date: Oct. 14, 2010

(65) Prior Publication Data

US 2012/0022120 A1 Jan. 26, 2012

(30) Foreign Application Priority Data

Apr. 9, 2009 (JP) ................................ 2009-111549
Apr. 9, 2009 (JP) ................................ 2009-111550

(51) Int. Cl.

| | |
|---|---|
| ***A61K 31/4178*** | (2006.01) |
| ***A61K 9/70*** | (2006.01) |
| ***A61K 9/00*** | (2006.01) |
| ***A61K 9/08*** | (2006.01) |

(52) U.S. Cl.

CPC ............ *A61K 9/7015* (2013.01); *A61K 9/0014* (2013.01); *A61K 9/08* (2013.01); *A61K 31/4178* (2013.01)

(58) Field of Classification Search

CPC combination set(s) only.
See application file for complete search history.

(56) References Cited

U.S. PATENT DOCUMENTS

| | | | | |
|---|---|---|---|---|
| 4,267,169 | A | 5/1981 | Kamishita et al. | |
| 4,636,520 | A | 1/1987 | Umio et al. | |
| 4,764,381 | A | 8/1988 | Bodor et al. | |
| 5,340,836 | A | 8/1994 | Reinhard et al. | |
| 5,461,068 | A | 10/1995 | Thaler et al. | |
| 5,690,923 | A | 11/1997 | De Vringer et al. | |
| 5,753,256 | A | 5/1998 | Cordes et al. | |
| 5,814,305 | A | 9/1998 | Laugier et al. | |
| 5,962,536 | A | 10/1999 | Komer | |
| 5,993,787 | A | 11/1999 | Sun et al. | |
| 6,007,791 | A | 12/1999 | Coombes et al. | |
| 6,008,256 | A | 12/1999 | Haraguchi et al. | |
| 6,017,920 | A | 1/2000 | Kamishita et al. | |
| 6,083,518 | A | 7/2000 | Lindahl | |
| 6,428,654 | B1 | 8/2002 | Cronan, Jr. et al. | |
| 6,585,963 | B1 | 7/2003 | Quan et al. | |
| 6,740,326 | B1 | 5/2004 | Meyer et al. | |
| 8,058,303 | B2 * | 11/2011 | Miki et al. | 514/397 |
| 2003/0017207 | A1 | 1/2003 | Lin et al. | |
| 2003/0235541 | A1 | 12/2003 | Maibach et al. | |
| 2004/0208906 | A1 | 10/2004 | Tatara et al. | |
| 2005/0232879 | A1 | 10/2005 | Sasagawa et al. | |
| 2006/0140984 | A1 | 6/2006 | Tamarkin et al. | |
| 2007/0099932 | A1 | 5/2007 | Shirouzu et al. | |
| 2008/0031835 | A1 | 2/2008 | Kawamura et al. | |
| 2008/0260656 | A1 | 10/2008 | Mallard | |
| 2009/0030059 | A1 | 1/2009 | Miki et al. | |
| 2009/0076109 | A1 | 3/2009 | Miki et al. | |
| 2009/0099202 | A1 | 4/2009 | Shirouzu et al. | |
| 2009/0137651 | A1 | 5/2009 | Kobayashi et al. | |

(Continued)

FOREIGN PATENT DOCUMENTS

| | | |
|---|---|---|
| EP | 0 070 525 | 1/1983 |
| EP | 0 440 298 | 8/1991 |

(Continued)

OTHER PUBLICATIONS

International Search Report dated Oct. 15, 2010 issued to international application No. PCT?JP2010/056884.

Borrás-Blasco, et al. "A Mathematical Approach to Predicting the Percutaneous Absorption Enhancing Effect of Sodium Lauryl Sulphate," *International Journal of Pharmaceutics*, vol. 269, pp. 121-129, 2004.

Uchida, et al. "In vitro Activity of Novel Imidazole Antifungal Agent NND-502 Against *Malassezia* Species," *International Journal of Antimicrobial Agents*, vol. 21, pp. 234-238, 2003.

(Continued)

*Primary Examiner* — Sreeni Padmanabhan
*Assistant Examiner* — Jody Karol
(74) *Attorney, Agent, or Firm* — Knobbe, Martens, Olson & Bear, LLP

(57) ABSTRACT

In a pharmaceutical composition for external use containing a compound such as luliconazole and/or a salt thereof, comprised are a higher alcohol which is in a liquid state at 1 atm and 25° C. and/or a diester of a dibasic acid, provided that a diester carbonate is excluded, and a polyoxyethylene alkyl ether and/or a polyoxyethylene alkenyl ether. Provided is a preparation using a solvent other than crotamiton, propylene carbonate, and N-methyl-2-pyrroridone as a solvent for solubilization and steric stabilization and having the following properties: 1) when a compound represented by the general formula (1) and/or a salt thereof has a stereoisomer, the amount of the stereoisomer of the compound and/or a salt thereof produced under a preservation condition of 60 degrees C. for 3 weeks is 1% by mass or less with respect to the total mass of the compound and/or a salt thereof at the beginning of preservation; 2) the preparation is in a clear liquid state when preserved at a constant temperature of 20° C. immediately after manufacture; and 3) no crystal is deposited when the preparation is preserved at 5° C. for 2 weeks after manufacture.

7 Claims, No Drawings

(56) References Cited

U.S. PATENT DOCUMENTS

| | | | |
|---|---|---|---|
| 2009/0202602 A1 | 8/2009 | Ishima et al. |
| 2010/0168200 A1 | 7/2010 | Masuda et al. |
| 2010/0173965 A1 | 7/2010 | Masuda et al. |
| 2010/0204293 A1 | 8/2010 | Masuda et al. |
| 2010/0210702 A1 | 8/2010 | Vontz et al. |
| 2010/0210703 A1 | 8/2010 | Vontz et al. |
| 2012/0014893 A1 | 1/2012 | Kobayashi et al. |
| 2012/0022120 A1 | 1/2012 | Kobayashi et al. |
| 2012/0149745 A1 | 6/2012 | Kobayashi et al. |
| 2013/0011351 A2 | 1/2013 | Kobayashi et al. |
| 2013/0090365 A1 | 4/2013 | Kubota et al. |
| 2014/0080882 A1 | 3/2014 | Masuda et al. |

FOREIGN PATENT DOCUMENTS

| | | |
|---|---|---|
| EP | 0 715 856 | 6/1996 |
| EP | 1 138 314 | 10/2001 |
| EP | 1 522 316 | 4/2005 |
| EP | 1 537 868 | 6/2005 |
| EP | 1 637 132 | 3/2006 |
| EP | 2 005 958 | 12/2008 |
| EP | 2 005 959 | 12/2008 |
| EP | 2 025 337 | 2/2009 |
| EP | 2 191 827 | 6/2010 |
| JP | 61-118315 | 6/1986 |
| JP | 62-093227 | 4/1987 |
| JP | 62-223163 | 10/1987 |
| JP | 01-242525 | 9/1989 |
| JP | 01-246219 | 10/1989 |
| JP | 02-264723 | 10/1990 |
| JP | 02-275877 | 11/1990 |
| JP | 05-306223 | 11/1993 |
| JP | 06-199701 | 7/1994 |
| JP | 06-211651 | 8/1994 |
| JP | 07-188027 | 7/1995 |
| JP | 07-206711 | 8/1995 |
| JP | 07-223971 | 8/1995 |
| JP | 08-020527 | 1/1996 |
| JP | 08-291049 | 11/1996 |
| JP | 10-152433 | 6/1998 |
| JP | 10-226639 | 8/1998 |
| JP | 10-226686 | 8/1998 |
| JP | 2001-064206 | 3/2001 |
| JP | 2001-316247 | 11/2001 |
| JP | 2002-114680 | 4/2002 |
| JP | 2002-193755 | 7/2002 |
| JP | 2002-284702 | 10/2002 |
| JP | 2002-363070 | 12/2002 |
| JP | 2003-252798 | 9/2003 |
| JP | 2004-529923 | 9/2004 |
| JP | 2005-154306 | 6/2005 |
| JP | 2005-239678 | 9/2005 |
| JP | 2005-289879 | 10/2005 |
| JP | 2005-298388 | 10/2005 |
| JP | 2005-298635 | 10/2005 |
| JP | 2006-028123 | 2/2006 |
| JP | 2006-232856 | 9/2006 |
| JP | 2006-306734 | 11/2006 |
| JP | 2007-091661 A | 4/2007 |
| JP | 2009-511553 | 3/2009 |
| RU | 2 270 894 C2 | 3/2004 |
| WO | WO 90/14094 | 11/1990 |
| WO | WO 95/30440 | 11/1995 |
| WO | WO 96/11710 | 4/1996 |
| WO | WO 96/40047 | 12/1996 |
| WO | WO 97/02821 | 1/1997 |
| WO | WO 97/07794 | 3/1997 |
| WO | WO 00/01384 | 1/2000 |
| WO | WO 02/062336 | 8/2002 |
| WO | WO 02/083084 | 10/2002 |
| WO | WO 02/087570 | 11/2002 |
| WO | WO 03/020248 | 3/2003 |
| WO | WO 03/105841 | 12/2003 |
| WO | WO 2004/021968 | 3/2004 |
| WO | WO 2004/084826 | 10/2004 |
| WO | WO 2004/091521 | 10/2004 |
| WO | WO 2006/038317 | 4/2005 |
| WO | WO 2005/099764 | 10/2005 |
| WO | WO 2005/123136 | 12/2005 |
| WO | WO 2007/042682 | 4/2007 |
| WO | WO 2007/102241 | 9/2007 |
| WO | WO 2007/102242 | 9/2007 |
| WO | WO 2007/077806 | 12/2007 |
| WO | WO 2008/075207 | 6/2008 |
| WO | WO 2009/031642 A1 | 3/2009 |
| WO | WO 2010/093992 | 8/2010 |
| WO | WO 2014/041708 A1 | 3/2014 |
| WO | WO 2014/041825 A1 | 3/2014 |
| WO | WO 2014/041846 A1 | 3/2014 |
| WO | WO 2014/042043 A1 | 3/2014 |
| WO | WO 2014/136282 | 9/2014 |

OTHER PUBLICATIONS

Uchida, et al. "In vitro Antifungal Activity of Luliconazole (NND-502), a Novel Imidazole Antifungal Agent," *Journal of Infectious Chemothererapy*, vol. 10, pp. 216-219, 2004.

Costa Martins, et al "In vitro Sensitivity of Dermatophytes to Urea," *Clinics*, vol. 61, No. 1, pp. 9-14, 2006.

www.babymd.com (available online as of Feb. 16, 2001 as evidenced by the attached Internet Archive report) accessed online Dec. 18, 2010.

Niwano, et al. "Efficacy of NND-502, a Novel Imidazole Antimycotic Agent, in Experimental Models of *Candida albicans* and *Aspergillus fumigatus* Infections," *International journal of Antimicrobial Agents*, vol. 12, pp. 221-228, 1999.

Niwano, et al. "In vitro and in vivo Antidermatophyte Activities of NND-4502, a Novel Optically Active Imidazole Antimycotic Agent," *Antimicrobial Agents and Chemotherapy*, vol. 42, No. 4, pp. 967-970, Apr. 1998.

GHS Classification Guidance for Enterprises (2$^{nd}$ Edition, Ministry of Economy, Trade and Industry, Japan, Mar. 2010.

Crotamiton Properties (http://www.chemspider.com/Chemical-Structure.2780.html) 2 pages.

Absolute ethanol MSDS (www.sciencelab.com/msds.php?msdsId=9923955) 7 pages.

Methyl Ethyl Ketone MSDS (www.sciencelab.com/msds.php?msdsId=9927358) 6 pages.

Niwano, et al. "Lanoconazole and Its Related Optically Active Compound NND-502: Novel Antifungal Imidazoles with a Ketene Dithioacetal Structure," *Current Medicinal Chemistry*, vol. 2, pp. 147-160, 2003.

Koga et al., "In vitro antifungal activities of luliconazole, a new topical imidazole," Med. Mycol., vol. 47(6), pp. 640-647 (2009).

Database WPI Week 200732, AN 2007-337919 and JP 2007-091661.

International Search Report dated Oct. 18, 2010 issued to international application No. PCT/JP2010/056881.

International Search Report dated Oct. 18, 2010 issued to international application No. PCT/JP2010/063230.

Vieira, et al. "Cationic Lipids and Surfactants as Antifungal Agents: Mode of Action," *Journal of Antimicrobial Chemotherapy*, Vo. 58, pp. 760-767, 2006.

SDS Density downloaded from www.chemicalbook.com/ChernicalProductPropertyEN_CB2147453.htm, 2 pages, copyright 2010.

Pluronics Density downloaded from www.chemicalbook.com/ChemicalProductPropertyEN_Cb2709101.htm, 2 pages, copyright 2010.

Ethyl Cellulose Density downloaded from www.chemicalbook.com/ProductMSDSDetailCB6165620_EN.htm, 3 pages, copyright 2008.

U.S. Appl. No. 14,263,293, Masuda et al.

U.S. Appl. No. 14/388,218, Masuda et al.

U.S. Appl. No. 14/419,864, Masuda et al.

* cited by examiner

ANTIMYCOTIC PHARMACEUTICAL COMPOSITION

CROSS-REFERENCE TO RELATED APPLICATIONS

This application is the U.S. National Phase under 35 U.S.C. §371 of International Application PCT/JP2010/056884, filed Apr. 9, 2010, which claims priority to JP Application No. 2009-111549, filed Apr. 9, 2009 and JP Application No. 2009-111550, filed Apr. 9, 2009.

TECHNICAL FIELD

The present invention relates to a pharmaceutical composition, and more particularly, to an antimycotic pharmaceutical composition for external use which is useful for treatment of mycoses.

BACKGROUND ART

A compound having a structure represented by the following general formula (1) has excellent antimycotic activity. Luliconazole is a compound having the structure represented by the general formula (1) where both of $R_1$ and $R_2$ are chlorine atoms. The compound having the structure represented by the following general formula (1) such as luliconazole has excellent antimycotic activity, and hence it has been pointed out that the compound is also applicable for treatment of onychomycosis, which has been considered to be untreatable by external application (e.g., see Patent document 1). However, in the case of producing a preparation for treating such onychomycosis, it has been desired to further increase the content of the compound represented by the general formula (1). In particular, in a preparation for treating tinea unguium, the compound represented by the general formula (1) has been desired to be solubilized in an amount twice or more the content of a general preparation for treating dermatomycosis, specifically, in an amount of 5% by mass or more, and it has been desired to develop a solvent to be used for solubilizing at a high concentration and formulating the compound represented by the general formula (1).

However, there was a situation in which only a few solvents could be used for producing a preparation containing such a compound at a high concentration because of its high crystallinity. That is, depending on the type of the solvent, there were some inconveniences, such as deposition of crystals at a low temperature such as 5° C. and deposition of crystals in application.

In addition, in a solution of luliconazole or the like, there exists a situation in which stereoisomers are easily produced. As a solvent to be used for preventing production of such stereoisomers, only crotamiton, propylene carbonate, and N-methyl-2-pyrroridone have been known (e.g., see Patent document 2). However, even such solvents have a problem such that blending has been limited in some cases depending on the inherent medicinal effects of the solvents, such as anti-inflammatory effects, and it has been desired to develop a novel solvent for formulation of luliconazole or the like as an alternative of the solvents.

General formula (1)

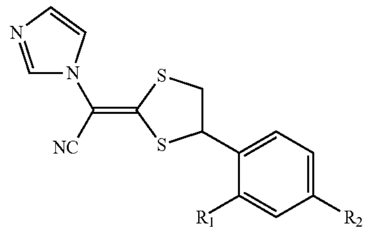

where $R_1$ and $R_2$ each independently represent a hydrogen atom or a halogen atom, and at least one of $R_1$ and $R_2$ represents a halogen atom.

That is, in other words, it has been desired to develop a preparation having the following properties, which is a pharmaceutical composition for external use containing luliconazole or the like using a solvent other than crotamiton, propylene carbonate, and N-methyl-2-pyrroridone for solubilization and steric stabilization:

1) an amount of a stereoisomer of luliconazole or the like produced under a preservation condition of 60° C. for 3 weeks is 1% by mass or less with respect to a total mass of luliconazole or the like at the beginning of preservation;

2) the preparation is in a clear liquid state when preserved at a constant temperature of 20° C. immediately after manufacture; and 3) no crystal is deposited when the preparation is preserved at 5° C. for 2 weeks after manufacture.

Meanwhile, a higher alcohol which is in a liquid state at 1 atm and 25° C., such as isostearyl alcohol, a polyoxyethylene alkyl (or alkenyl)ether, and a diester of a dibasic acid such as diisopropyl adipate are known as components for drug formulation. Examples of a medicinal preparation containing the components in combination include ointments (e.g., see Patent document 3) and gels (e.g., see Patent documents 4, 5, 6, and 7). However, no solution-based preparation is known, and there is no example of their use for maintaining the steric structure of a compound.

[Patent document 1] WO 2007/102241
[Patent document 2] WO 2007/102242
[Patent document 3] JP 08-291049 A
[Patent document 4] JP 2005-298635 A
[Patent document 5] JP 2005-298388 A
[Patent document 6] JP 2006-232856 A
[Patent document 7] JP 2005-239678 A

SUMMARY OF THE INVENTION

Technical Problem

The present invention has been made under such circumstances, and an object of the present invention is to provide a pharmaceutical composition for external use containing a compound represented by the general formula (1) and/or a salt thereof, such as luliconazole, which is a preparation using a solvent other than crotamiton, propylene carbonate, and N-methyl-2-pyrroridone as a solvent for solubilization and steric stabilization and having the following properties 2) and 3). Another object of the present invention is to provide a preparation having the following properties 1) to 3) in the case where the compound represented by the general formula (1) and/or a salt thereof has a stereoisomer:

1) an amount of a stereoisomer of the compound and/or a salt thereof produced under a preservation condition of 60° C. for 3 weeks is 1% by mass or less with respect to a total mass of the compound and/or a salt thereof at the beginning of preservation;

2) the preparation is in a clear liquid state when preserved at a constant temperature of 20° C. immediately after manufacture; and 3) no crystal is deposited when the preparation is preserved at 5° C. for 2 weeks after manufacture.

Solution to Problem

In consideration of such circumstances, the inventors of the present invention have made intensive studies and efforts to provide a pharmaceutical composition for external use containing a compound represented by the general formula (1) and/or a salt thereof, which is a liquid preparation where the compound represented by the general formula (1) and/or a salt thereof is stabilized at a high or low temperature by using a solvent other than crotamiton, propylene carbonate, and N-methyl-2-pyrroridone. As a result, the inventors have finally completed the present invention by finding out that combination use of a higher alcohol which is in a liquid state at 1 atm and 25° C. and/or a diester of a dibasic acid and a polyoxyethylene alkyl (or alkenyl)ether enables provision of such a preparation. In other words, the present invention is as follows. Note that the dibasic acid is a general name including a dicarboxylic acid having two carboxyl groups and excludes carbonic acids.

[1] A pharmaceutical composition for external use, including: 1) a compound represented by the following general formula (1) and/or a salt thereof; 2) at least one kind selected from a higher alcohol which is in a liquid state at 1 atm and 25° C. and a diester of a dibasic acid, provided that a diester carbonate is excluded; and 3) at least one kind selected from a polyoxyethylene alkyl ether and a polyoxyethylene alkenyl ether;

General formula (1)

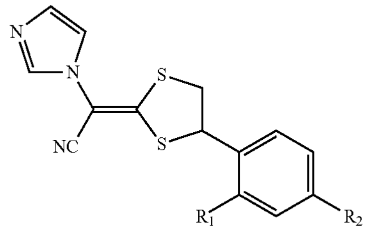

where $R_1$ and $R_2$ each independently represent a hydrogen atom or a halogen atom, and at least one of $R_1$ and $R_2$ represents a halogen atom.

[2] A pharmaceutical composition for external use according to the item [1], in which the compound represented by the general formula (1) is luliconazole.

[3] A pharmaceutical composition for external use according to the item [1] or [2], in which at least one kind selected from the higher alcohol which is in a liquid state at 1 atm and 25° C. and the diester of a dibasic acid is isostearyl alcohol and/or diisopropyl adipate, and at least one kind selected from the polyoxyethylene alkyl ether and the polyoxyethylene alkenyl ether is polyoxyethylene lauryl ether and/or polyoxyethylene cetyl ether.

[4] A pharmaceutical composition for external use according to any one of the items [1] to [3], which has the following properties:

1) when the compound represented by the general formula (1) and/or a salt thereof has a stereoisomer, an amount of the stereoisomer of the compound and/or a salt thereof produced under a preservation condition of 60° C. for 3 weeks is 1% by mass or less with respect to a total mass of the compound and/or a salt thereof at the beginning of preservation;

2) the composition is in a clear liquid state when preserved at a constant temperature of 20° C. immediately after manufacture; and 3) no crystal is deposited when the composition is preserved at 5° C. for 2 weeks after manufacture.

[5] A pharmaceutical composition for external use according to any one of the items [1] to [4], further including at least one solvent selected from a diester carbonate, crotamiton, and N-methyl-2-pyrrolidone.

[6] A pharmaceutical composition for external use according to any one of the items [1] to [5], wherein the pharmaceutical composition is a medicament for treatment of tinea unguium.

[7] A solubilizer for a compound represented by the following general formula (1) and/or a salt thereof, including a mixture of: 1) at least one kind selected from a higher alcohol which is in a liquid state at 1 atm and 25° C. and a diester of a dibasic acid, provided that a diester carbonate is excluded; and 2) at least one kind selected from a polyoxyethylene alkyl ether and a polyoxyethylene alkenyl ether;

General formula (1)

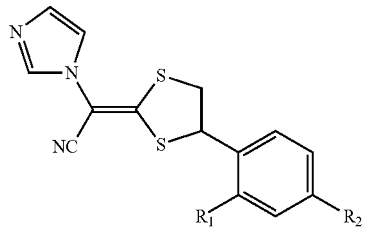

where $R_1$ and $R_2$ each independently represent a hydrogen atom or a halogen atom, and at least one of $R_1$ and $R_2$ represents a halogen atom.

[8] A solubilizer according to the item [7], including a mixture of at least one kind selected from the higher alcohol which is in a liquid state at 1 atm and 25° C. and the diester of a dibasic acid and at least one kind selected from the polyoxyethylene alkyl ether and the polyoxyethylene alkenyl ether at a mass ratio of 4:1.

[9] A solubilizer according to the item [7] or [8], in which the compound represented by the general formula (1) is luliconazole, and the solubilizer is for steric stabilization of luliconazole.

[10] A method of manufacturing the pharmaceutical composition for external use according to any one of the items [1] to [6], comprising the steps of: dampening a compound represented by the general formula (1) and/or a salt thereof with a part of a solvent; after the previous process, adding components except a higher alcohol which is in a liquid state at 1 atm and 25° C., a diester of a dibasic acid, provided that a diester carbonate is excluded, a polyoxyethylene alkyl ether and a polyoxyethylene alkenyl ether; and after the previous process, adding at least one kind selected from the higher alcohol which is in a liquid state at 1 atm and 25° C. and the diester of a dibasic acid, provided that a diester carbonate is excluded, and at least one kind selected from the polyoxyethylene alkyl ether and the polyoxyethylene alkenyl ether.

Advantageous Effects of Invention

The present invention can provide a pharmaceutical composition for external use containing a compound represented by the general formula (1) and/or a salt thereof, such as luliconazole, which is a preparation using a solvent other than crotamiton, propylene carbonate, and N-methyl-2-pyrroridone as a solvent for solubilization and steric stabilization and having the following properties 2) and 3). Further, the present invention can provide a preparation having the following properties 1) to 3) in the case where the compound represented by the general formula (1) and/or a salt thereof has a stereoisomer:

1) an amount of a stereoisomer of the compound and/or a salt thereof produced under a preservation condition of 60° C. for 3 weeks is 1% by mass or less with respect to a total mass of the compound and/or a salt thereof at the beginning of preservation;

2) the preparation is in a clear liquid state when preserved at a constant temperature of 20° C. immediately after manufacture; and 3) no crystal is deposited when the preparation is preserved at 5° C. for 2 weeks after manufacture.

DESCRIPTION OF EMBODIMENTS

<1> Compound Represented by the General Formula (1) and/or Salt Thereof as Essential Component of Pharmaceutical Composition for External Use of the Present Invention The pharmaceutical composition for external use of the present invention is characterized by including a compound represented by the general formula (1) and/or a salt thereof, such as luliconazole and lanoconazole. Luliconazole is a compound represented by the chemical name (R)—(−)-(E)-[4-(2,4-dichlorophenyl)-1,3-dithiolane-2-ylidene]-1-imidazolylacetonitrile, and lanoconazole is a compound represented by the chemical name (±)-(E)-[4-(2-chlorophenyl)-1,3-dithiolane-2-ylidene]-1-imidazolylacetonitrile. Methods of producing those compounds have already been known (see, for example, JP 09-100279 A).

The pharmaceutical composition for external use of the present invention is characterized by containing the compound represented by the general formula (1) and/or a salt thereof at a concentration of, generally 1 to 15% by mass, preferably 5 to 13% by mass with respect to the total amount of the pharmaceutical composition. The compound represented by the general formula (1) and/or a salt thereof has high crystallinity and may cause deposition of crystals when preserved at a low temperature such as 5° C. in the case where the composition is contained at a concentration of 1% by mass or more, depending on the type of a solvent used, even in a state where crystallization is suppressed by adding a hydroxycarboxylic acid such as lactic acid. In the present invention, such deposition is suppressed by a combination of the below-mentioned solvents of a higher alcohol which is in a liquid state at 1 atm and 25° C. and/or a diester of a dibasic acid, and a polyoxyethylene alkyl (or alkenyl)ether and thereby its bioavailability, in particular, transference into the nail is enhanced and as a result a therapeutic effect for tinea unguium is enhanced. The nail is an organ where transference into the tissue is difficult, and in order to transfer an effective amount of a compound, the content is preferably 1% by mass or more, more preferably 5% by mass or more with respect to the total amount of the pharmaceutical composition. Meanwhile, in view of the upper limit for suppressing deposition of crystals at a low temperature, the content is preferably 15% by mass or less, more preferably 13% by mass or less with respect to the total amount of the pharmaceutical composition. The facts indicate that the content is more preferably about 5 to 13% by mass.

The above-mentioned “salt thereof” is not specifically limited as far as it is physiologically acceptable. Preferred examples thereof include: mineral acid salts such as hydrochloride, nitrate, sulfate, and phosphate; organic acid salts such as citrate, oxalate, lactate, and acetate; and sulfuric acid-containing salts such as mesilate and tosilate. In terms of safety and solubility, hydrochloride is more preferred.

<2> Higher Alcohol and Diester of Dibasic Acid as Essential Components of Pharmaceutical Composition for External Use of the Present Invention The pharmaceutical composition for external use of the present invention is characterized by including a higher alcohol and/or a diester of a dibasic acid as an essential component. Here, the dibasic acid refers to a dicarboxylic acid having two carboxyl groups and does not include a carbonic acid. Higher alcohols which may be used include those that are in a liquid state under a condition of 1 atm and 25° C. Examples of the compounds exhibiting such properties suitably include branched higher alcohols having 10 to 30 carbon atoms and unsaturated alcohols having 10 to 30 carbon atoms. Specific examples thereof suitably include isostearyl alcohol, isocetyl alcohol, and oleyl alcohol, of which isostearyl alcohol is preferred. Further, examples of dibasic acids constituting diesters of dibasic acids include dibasic acids having for example, 2 to 10 carbon atoms, preferably, those having 4 to 8 carbon atoms. Specific examples thereof suitably include adipic acid, succinic acid, and sebacic acid. Examples of esters constituting diesters of dibasic acids include linear or branched alkyl esters or alkenyl esters having for example, 1 to 20 carbon atoms, preferably, those having 1 to 5 carbon atoms. Specific examples thereof suitably include an ethyl ester, a propyl ester, an isopropyl ester, and a butyl ester. The diester of the dibasic acid may include only one kind of ester or a combination of two or more kinds of esters. Preferred specific examples of diesters of dibasic acids include diethyl adipate, dipropyl adipate, diethyl succinate, dipropyl succinate, diisopropyl succinate, diethyl sebacate, dipropyl sebacate, and diisopropyl sebacate.

These components suppress deposition of crystals of the compound represented by the general formula (1) and/or a salt thereof at a low temperature region. In addition, the components increase solubility of the compound itself. In order to achieve such effects, for example, the higher alcohol which is in a liquid state under a condition of 1 atm and 25° C. may be contained at a concentration of, generally 10 to 30% by mass, preferably 15 to 25% by mass, more preferably 20% by mass with respect to the total amount of the pharmaceutical composition. On the other hand, the diester of a dibasic acid may be contained at a concentration of, generally 5 to 30% by mass, preferably 10 to 25% by mass, more preferably 12% by mass with respect to the total amount of the pharmaceutical composition.

For the higher alcohol which is in a liquid state under a condition of 1 atm and 25° C. or the diester of a dibasic acid, there may be selected a single kind thereof or a combination of two or more kinds thereof. Although each of the amounts may be independently in a preferred range selected, the total of the masses of the two components is preferably 5 to 30% by mass, more preferably 10 to 25% by mass with respect to the total amount of the pharmaceutical composition.

<3> Polyoxyethylene Alkyl (or Alkenyl)Ether as Essential Component of Pharmaceutical Composition for External Use of the Present Invention The pharmaceutical composition for external use of the present invention is characterized by containing a polyoxyethylene alkyl ether and/or a polyoxyethylene alkenyl ether as an essential component. In a polyoxyethylene group constituting the polyoxyethylene alkyl (or alkenyl)ether, the polymerization degree of oxyethylene is preferably 1 to 30, more preferably 2 to 25. As for the properties, the polyoxyethylene alkyl (or alkenyl)ether is preferably in a liquid state under a condition of 1 atm and 25° C. In an alkyl group or alkenyl group constituting the polyoxyethylene alkyl (or alkenyl) ether, the number of carbon atoms is 8 or more, preferably 10 to 30, particularly preferably 10 to 18. Specifically, examples thereof particularly suitably include a lauryl group, a cetyl group, an isostearyl group, and an oleyl group. Specific preferred examples of the polyoxyethylene alkyl (or alkenyl) ether include polyoxyethylene (POE) (4.2) lauryl ether, POE (10) cetyl ether, POE (30) cetyl ether, POE (10) oleyl ether, and POE (20) isostearyl ether.

Such components have effects of maintaining the solubilized state of the compound represented by the general formula (1) and/or a salt thereof stably in a high concentration region of 5% by mass or more even in a low temperature region of about 5° C. without impairing its steric stability in the dissolved state. To achieve such effects, each of the components may be contained, for example, at a concentration of generally 1 to 30% by mass, preferably 5 to 20% by mass, particularly preferably 5 to 15% by mass with respect to the total amount of the pharmaceutical composition. In particular, in the case where the content of the compound represented by the general formula (1) and/or a salt thereof is about 10% by mass, the effects are remarkably exerted by blending the component in an amount equal to or larger than the mass of the compound represented by the general formula (1) and/or a salt thereof. Therefore, it is preferred to satisfy such blending condition. Under such condition, the liquid state of the pharmaceutical composition for external use of the present invention is stable in liquid state when preserved for 2 weeks, preferably 1 month or more, particularly preferably 3 months or more at wide ranges of temperatures, including a low temperature region of about 5° C., a room temperature condition of 20° C., and a high temperature region of about 40° C. Very few stereoisomers are produced, and even after preservation at 60° C. for 3 weeks, the amount of the stereoisomers is 1% by mass or less with respect to the total mass of the compound at the beginning of preservation. Therefore, the composition is preferred as a preparation for an organ with low absorbability such as the nail. In particular, deposition of crystals is hardly caused by evaporation after application, and hence absorption to the nail is not inhibited. Such effect may significantly improve its bioavailability.

For the polyoxyethylene alkyl (or alkenyl)ether, there may be selected a single kind thereof or a combination of two or more kinds thereof.

In the pharmaceutical composition for external use of the present invention, the mass ratio of the higher alcohol which is in a liquid state at 1 atm and 25° C. such as isostearyl alcohol and/or the diester of a dibasic acid such as diisopropyl adipate, and the polyoxyethylene alkyl (or alkenyl)ether is preferably 7:1 to 1:1, more preferably 6:1 to 12:5. The mass ratio of the higher alcohol which is in a liquid state at 1 atm and 25° C. and the polyoxyethylene alkyl (or alkenyl)ether is preferably 5:1 to 1:1, particularly preferably 4:1. The mass ratio of the diester of a dibasic acid and the polyoxyethylene alkyl (or alkenyl)ether is preferably 7:1 to 1:1, and in the case of polyoxyethylene cetyl ether, the mass ratio is preferably 7:1 to 1:1, particularly preferably 6:1. In the case of the polyoxyethylene lauryl ether, the mass ratio is preferably 4:1 to 1:1, particularly preferably 12:5. Such content ratios provide excellent solvent effects for luliconazole or the like, and at the same time exert the effect of maintaining the steric structure in high-temperature preservation. The solvent effects lead to the effects of not only suppressing deposition of crystals in static preservation at about 5° C. but also suppressing deposition of crystals caused by impact, such as deposition of crystals during an application to the nail.

<4> Pharmaceutical Composition for External Use of the Present Invention

The pharmaceutical composition for external use of the present invention contains the above-mentioned essential components and may contain an optional component which is generally used for formulation.

Preferred examples of such an optional component include: oils and waxes such as macadamia nut oil, avocado oil, corn oil, olive oil, rapeseed oil, sesame oil, castor oil, safflower oil, cottonseed oil, jojoba oil, coconut oil, palm oil, liquid lanolin, hydrogenated coconut oil, hydrogenated oil, haze wax, hydrogenated castor oil, beeswax, candelilla wax, carnauba wax, insect wax, lanolin, reduced lanolin, hard lanolin, and jojoba wax; hydrocarbons such as liquid paraffin, squalane, pristane, ozokerite, paraffin, ceresin, vaseline, and microcrystalline wax; higher fatty acids such as oleic acid, isostearic acid, lauric acid, myristic acid, palmitic acid, stearic acid, behenic acid, and undecylenic acid; lower alcohols such as ethanol and isopropanol; higher alcohols such as oleyl alcohol, cetyl alcohol, stearyl alcohol, behenyl alcohol, octyldodecanol, myristyl alcohol, and cetostearyl alcohol; synthetic ester oils such as cetyl isooctanoate, isopropyl myristate, hexyldecyl isostearate, cetyl lactate, diisostearyl malate, ethylene glycol di-2-ethyl hexanoate, neopentyl glycol dicaprate, glycerin di-2-heptyl undecanoate, glycerin tri-2-ethylhexanoate, trimethylolpropane tri-2-ethyl hexanoate, trimethylolpropane triisostearate, and pentane erythrite tetra-2-ethylhexanoate; oils such as silicone oils which are not classified into silicones, including dimethyl polysiloxane, methylphenyl polysiloxane, and modified polysiloxanes such as amino-modified polysiloxane, polyether-modified polysiloxane, alkyl-modified polysiloxane, and fluorine-modified polysiloxane; anionic surfactants such as fatty acid soaps (including sodium laurate and sodium palmitate), potassium lauryl sulfate, triethanolamine alkyl ether sulfate, and sodium polyoxyethylene lauryl phosphate; cationic surfactants such as stearyltrimethylammonium chloride, benzalkonium chloride, and laurylamine oxide; amphoteric surfactants such as imidazoline-based amphoteric surfactants (including a 2-cocoyl-2-imidazolinium hydroxide-1-carboxyethyloxy-2-sodium salt), betaine-based amphoteric surfactants (including alkyl betaine, amide betaine, and sulfobetaine), and acylmethyl taurine; nonionic surfactants such as sorbitan fatty acid esters (including sorbitan monostearate, sorbitan monolaurate, and sorbitan sesquioleate), glycerin fatty acids (including glycerin monostearate), propylene glycol fatty acid esters (including propylene glycol monostearate), hydrogenated castor oil derivatives, glycerin alkyl ethers, POE sorbitan fatty acid esters (including POE sorbitan monooleate, polyoxyethylene sorbitan monostearate, and polyoxyethylene sorbitan monolaurate), POE sorbit fatty acid esters (including POE-sorbitan monolaurate), POE glycerin fatty acid esters (including POE-glycerin monoisostearate), POE fatty acid esters (including polyethylene glycol monooleate and POE distearate), POE alkylphenyl ethers (including POE octylphenyl ether and POE nonylphenyl ether), Pluronics, POE.POP alkyl ethers (including POE.POP2-decyltetradecyl ether), Tetronics, POE castor oil.hydrogenated castor oil derivatives (including POE castor oil and POE hydrogenated castor oil), sucrose fatty esters, and alkylglycosides; polyalcohols such as polyethylene glycol, glycerin, 1,3-butylene glycol, erythritol, sorbitol, xylitol, maltitol, glucono lactone, propylene glycol, dipropylene glycol, diglycerin, isoprene glycol, 1,2-pentanediol, 2,4-hexanediol, 1,2-hexanediol, 1,2-octanediol, polypropylene glycol, and 2-ethyl-1,3-hexanediol; moisture components such as sodium pyrrolidone carboxylate, lactic acid, and sodium lactate; pH adjusters such as phosphoric acid and citric acid; powders such as mica, talc, kaolin, synthetic mica, and barium sulfate which may have treated surfaces; inorganic pigments such as colcothar, yellow iron oxide, black iron oxide, cobalt oxide, ultramarine blue pigment, iron blue pigment, titanium oxide, and zinc oxide which may have treated surfaces; pearls such as mica titanium, fish scale guanine, and bismuth oxychloride which may have treated surfaces; organic pigments such as Red 202, Red 228, Red 226, Yellow 4, Blue 404, Yellow 5, Red 505, Red 230, Red 223, Orange 201, Red 213, Yellow 204, Yellow 203, Blue 1, Green 201, Violet 201, and Red 204 which may be laked; organic powders such as polyethylene powder, methyl polymethacrylate powder, nylon powder, and organopolysiloxane elastomer; UV absorbers such as p-aminobenzoic acid-based UV absorber, anthranilic acid-based UV absorber, salicylic acid-based UV absorber, cinnamic acid-based UV absorber, benzophenone-based UV absorber, sugar-based UV absorber, 2-(2'-hydroxy-5'-t-octylphenyl) benzotriazole, and 4-methoxy-4'-t-butyl dibenzoylmethane; vitamins such as vitamin A or derivatives thereof, vitamin Bs including vitamin $B_6$ hydrochloride, vitamin $B_6$ tripalmitate, vitamin $B_6$ dioctanoate, vitamin $B_2$ or derivatives thereof, vitamin $B_{12}$, and vitamin $B_{15}$ or derivatives thereof, vitamin Es including $\alpha$-tocopherol, $\beta$-tocopherol, $\gamma$-tocopherol, and vitamin E acetate, vitamin Ds, vitamin H, pantothenic acid, pantethine, and pyrroloquinoline quinone; solvents such as acetone, aromatic alcohols such as benzyl alcohol, phenylethyl alcohol, and phenylpropyl alcohol, crotamiton, N-methyl-2-pyrrolidone, alkylene carbonates such as ethylene carbonate, and propylene carbonate, diester carbonates such as diethyl carbonate and dicapryl carbonate, triacetin, and ethylene glycol salicylate; stabilizers such as hydroxylic acids such as lactic acid, glycolic acid, and citric acid, and mineral acids such as phosphoric acid; and the like.

Of such optional components, a solvent selected from an alkylene carbonate which has a cyclic structure such as propylene carbonate, a diester carbonate represented by dialkyl carbonates such as dicapryl carbonate which has a structure that two linear hydrocarbone groups are bonded, and an aromatic alcohol such as benzyl alcohol can be particularly preferably exemplified.

To improve the stability, the pharmaceutical composition for external use of the present invention preferably contains a diester carbonate such as a dialkyl carbonate or a alkylene carbonate, preferably the alkylene carbonate, more preferably propylene carbonate at a concentration of preferably 1 to 10% by mass, more preferably 2 to 8% by mass, particularly preferably 3 to 5% by mass with respect to the total amount of the pharmaceutical composition. In the diester carbonate, the total number of carbon atoms is preferably 5 to 30, more preferably 6 to 25. The component has the effect of improving solubilization stability of luliconazole or the like at a low temperature and the effect of suppressing deposition of crystals during preservation at 5° C. for 2 weeks, preferably 4 weeks or more and the effect of improving stability at a high temperature. The component prevents stereoisomerization even during preservation at 60° C. for 3 weeks and suppresses production of a stereoisomer to 1% by mass or less. The component is preferably contained at a mass ratio almost equal to or almost half of that of luliconazole or the like. Propylene carbonate is one of the alkylene carbonates, and another alkylene carbonate such as ethylene carbonate is within the technical scope of the present invention because it has the same effect as propylene carbonate. Alternatively, a diester carbonate such as diethyl carbonate or dicapryl carbonate is also within the technical scope of the present invention because it has the same effect as propylene carbonate. In the case of using two or more of the components, the amount of the diester carbonate may be converted into the total amount of the diester carbonates.

For the purpose of improving solubility and stability, the pharmaceutical composition for external use of the present invention contains an aromatic alcohol, preferably benzyl alcohol at a concentration of preferably 1 to 10% by mass, more preferably 1 to 8% by mass, particularly preferably 1 to 5% by mass with respect to the total amount of the pharmaceutical composition. The component is useful as an auxiliary agent for solubilizing the compound represented by the general formula (1) and/or a salt thereof in the manufacture, and has the effect of suppressing deposition of crystals of the compound represented by the general formula (1) and/or a salt thereof in low-temperature preservation. Such an effect is exerted when the amount is in the above-mentioned range. Another aromatic alcohol such as phenylethyl alcohol or phenylpropyl alcohol also provides a similar effect although the effect is lower than that of benzyl alcohol, and hence it can be used in the same way as benzyl alcohol. That is, such an aromatic alcohol is within the technical scope of the present invention.

For the carbonate diester and aromatic alcohol, there may be selected a single kind thereof or a combination of two or more kinds thereof. Although each of the amounts may be independently in a preferred range selected, the two components are preferably blended so that the total of the masses of the two components is 1 to 20% by mass, more preferably 2 to 18% by mass with respect to the total amount of the pharmaceutical composition.

To improve the stability of the pharmaceutical composition for external use of the present invention and the effect of suppressing deposition of crystals caused after application, a stabilizer such as a hydroxylic acid including lactic acid, glycolic acid, and citric acid or a mineral acid including phosphoric acid is preferably contained at a concentration of preferably 0.1 to 20% by mass, more preferably 1 to 10% by mass with respect to the total amount of the pharmaceutical composition. In addition, crotamiton or N-methyl-2-pyrroridone having the effect of maintaining steric stability is preferably contained at a concentration of preferably 1 to 30% by mass, more preferably 2 to 15% by mass with respect to the total amount of the pharmaceutical composition.

The pharmaceutical composition for external use of the present invention can be manufactured by using such optional components and essential components. Preferred examples of a method of manufacturing the pharmaceutical composition for external use of the present invention include a method involving adding part of a solvent component such as an aromatic alcohol or an aliphatic (lower) alcohol to a compound represented by the general formula (1) or a salt thereof to solvate the component and adding the residual solvent for solvation to solubilize the component. Preferred examples of the above-mentioned solvent for solvation and solubilization include an aliphatic (lower) alcohol or aromatic alcohol, and a solvent such as acetone, a diester carbonate, an aliphatic (higher) alcohol and a diester of a dibasic acid are preferably used for improving solubility. In such a solubilization process, heating is preferably performed at 30 to 90° C. The amount of the above-mentioned solvent for solvation is preferably 6 to 50% by mass of the total amount of the solvent for solvation. The pharmaceutical composition for external use of the present invention can be obtained by performing the above-mentioned processes and treating the resultant according to a conventional method.

The pharmaceutical composition for external use of the present invention can be formulated into any of forms without any limitations as far as the forms are used for any pharmaceutical composition for external use, and preferred examples thereof include lotions, emulsions, gelatinizing agents, cream pharmaceuticals, aerosols, nail enamel agents, and hydrogel patches. Of those, the lotions are particularly preferred.

The pharmaceutical composition for external use of the present invention is preferably used for treating mycotic diseases or preventing progression of the diseases by using characteristics of luliconazole or the like. For the mycotic diseases, there are exemplified: tinea pedis such as athlete's foot; tinea corporis such as candida and pityriasis versicolor; and tinea on a hard keratin portion, such as tinea unguium. Because of remarkable effects, it is particularly preferred to use the pharmaceutical composition for external use of the present invention for treating the hard keratin portion, such as tinea unguium. In particular, the pharmaceutical composition for external use of the present invention exerts a preferred effect on the nail, and such effect is also exerted on typical dermatomycosis. Therefore, a pharmaceutical composition for external use for dermatomycosis, which satisfies the configuration of the present invention, also falls within the technical scope of the present invention. For such dermatomycosis, there is exemplified tinea such as tinea pedis, particularly horny-outgrowing type hyperkeratotic tinea which appears on heels or the like. The present invention has a significant effect on hyperkeratotic tinea, on which the conventional agents hardly exert their effects, in the above-mentioned dermatomycosis, which is preferred.

With regard to its use, for example, the pharmaceutical composition is applied to a diseased portion one or several times a day at a preferred amount, and the treatment is preferably carried out day after day. In particular, for tinea unguium, luliconazole or the like, which is an effective component, can be transferred into the nail in an amount that cannot be attained by a normal formulation. Therefore, tinea unguium can be treated only by the external application without having to drink an antimycotic agent over a long period of time. In addition, recurrence and reinfection have been a major problem for tinea unguium. However, the recurrence and reinfection can be prevented by application of the pharmaceutical composition for external use of the present invention for 1 to 2 weeks after abatement of the symptom. The pharmaceutical composition for external use of the present invention exerts preventive efficacy in this aspect.

As described above, the pharmaceutical composition for external use of the present invention may be a preparation having the following properties 2) and 3). The pharmaceutical composition may also be a preparation having the following properties 1) to 3) in the case where the compound represented by the general formula (1) and/or a salt thereof has a stereoisomer:

1) the amount of a stereoisomer of the compound and/or a salt thereof produced under a preservation condition of 60° C. for 3 weeks is 1% by mass or less with respect to the total mass of the compound and/or a salt thereof at the beginning of preservation.

2) the preparation is in a clear liquid state when preserved at a constant temperature of 20° C. immediately after manufacture.

3) no crystal is deposited when the preparation is preserved at 5° C. for 2 weeks after manufacture.

The property 1) can be determined by, for example, preserving the preparation at 60° C. for 3 weeks after manufacture, performing liquid chromatography using an optically-active stationary phase which can separate a compound of interest from an optical isomer thereof to optically resolve the compound from the optical isomer, and calculating the amount of the isomer by a peak area of the optical isomer in the resultant chart.

The property 2) can be judged by, for example, maintaining the preparation after manufacture at a constant temperature of 20° C. and observing the state of the liquid with the naked eye and/or under a microscope when/after the temperature of the preparation is constant. In the case where white turbidity, precipitation, or the like is not observed, the preparation is judged as a clear liquid.

The property 3) can be judged by, for example, preserving the preparation at 5° C. for 2 weeks after manufacture and observing the preparation with the naked eye and/or under a microscope. In the case where deposition of crystals is not observed with the naked eye and/or under a microscope, the preparation is judged to cause no deposition of crystals.

The thus-obtained pharmaceutical composition for external use of the present invention has an excellent effect of maintaining its transparency over a long period of time although the composition contains a high concentration of a compound represented by the general formula (1) and/or a salt thereof. In addition, because deposition of crystals after application is suppressed, inhibition of orientation and transfer of the compound to organs by the crystals is suppressed. Therefore, the composition has excellent bioavailability. Meanwhile, a sufficient amount of the compound is oriented to an organ with low drug orientation such as the nail, and hence the composition is preferred as a pharmaceutical composition for external use for the nail.

<5> Solubilizer of Present Invention

The solubilizer of the present invention is characterized by containing a mixture of 1) at least one kind selected from a higher alcohol which is in a liquid state at 1 atm and 25° C. and/or a diester of a dibasic acid, provided that a diester carbonate is excluded, and at least one kind selected from a polyoxyethylene alkyl ether and a polyoxyethylene alkenyl ether. The kind and content ratio of the higher alcohol which is in a liquid state at 1 atm and 25° C., diester of a dibasic acid, polyoxyethylene alkyl ether, and polyoxyethylene alkenyl ether may be the same as those described in the above-mentioned item for the pharmaceutical composition for external use of the present invention.

The solubilizer of the present invention has the steric stabilization effect of a compound represented by the general formula (1) and/or a salt thereof, which has a stereoisomer, such as luliconazole. The solubilizer can be used as one having the steric stabilization effect of such compound.

EXAMPLES

Hereinafter, the present invention is described in more detail by way of examples.

Example 1 and Reference Examples 1 and 2

According to the following formulation, the pharmaceutical composition for external use of the present invention was prepared. That is, components A and B were separately mixed and heated to 65° C., and solubilization of the components B was confirmed. The mixture B was gradually added to the mixture A with stirring, and the resultant mixture was further stirred, followed by confirmation of solubilization. To the mixture were gradually added components C, which had been mixed and heated to 65° C., with stirring, and solubilization was confirmed. To the resultant mixture were added components D, which had been heated to 65° C. to solubilize, followed by mixing with stirring, and solubilization was confirmed. The mixture was cooled with stirring, to thereby obtain Pharmaceutical composition 1 for external use. The composition was preserved at 20° C. for 12 hours and then observed with the naked eye and under a microscope. The deposition of crystals was not observed with the naked eye and under a microscope, and was in a clear liquid state.

According to the formulation of Example 1, except that diisopropyl adipate is used instead of isostearyl alcohol and Polyoxyethylene (4.2) lauryl ether, the composition of Reference Example 1 was intended to be prepared in the same way in Example 1. However, extreme deposition of crystals was observed during a procedure of mixing with stirring. Further, the composition of Reference Example 2 having a reducing amount of Luliconazole in the formulation of Reference Example 1 was prepared utilizing the formulation of Reference Example 1 with an alteration of the amount of Luliconazole from 5% by mass to 2% by mass. The deposition of crystals was observed after the preservation at 5° C. for 1 week. When the composition of Reference Example 2 immediately after preparation was applied to a nail, crystals were deposited in an extent of being observed with the naked eye. From these results, it can be understood that in the composition of Example 1, suppression of deposition of crystals in the preparation and just after an application is provided by adding isostearyl alcohol and Polyoxyethylene (4.2) lauryl ether.

TABLE 1

| Component | % by mass |
|---|---|
| A | |
| Luliconazole | 5 |
| Benzyl alcohol | 1 |
| Ethanol | 4 |
| B | |
| Benzyl alcohol | 1 |
| Lactic acid | 4 |
| Ethanol | 30 |
| C | |
| Isostearyl alcohol | 20 |
| Polyoxyethylene (4.2) lauryl ether | 5 |
| D | |
| Propylene glycol | 10 |
| Polyethylene glycol 400 | 20 |
| Total | 100 |

<Characteristics of Pharmaceutical Composition 1 for External Use>

(1) Stability at 60° C.

Pharmaceutical composition 1 for external use was preserved at 60° C. for 3 weeks, and the content of luliconazole and the content of its stereoisomer were measured by an HPLC method. The quantitative value of luliconazole was 100%, and the SE form [(S)-(+) form] content and the Z form content were 0.38% by mass and 0.05% by mass, respectively. The values are substantially equal to the values determined immediately after manufacture (quantitative value; 100% by mass, SE form; 0.32% by mass, Z form; 0.05% by mass).

A method for quantifying an SE form is as follows: HPLC (manufactured by Shimadzu Corporation LC-9A system, HPLC conditions: column; CHIRALCEL OD-R 4.6×250 mm, column temperature; 40° C., mobile phase; a sodium perchlorate mixture (methanol/water (4:1, v/v)) solution (7→500), flow rate; 0.56 mL/min., detection; 295 nm)

Meanwhile, a method for quantifying a Z form is as follows: HPLC (manufactured by Shimadzu Corporation LC-10VP system, HPLC conditions: column; Inertsil ODS-2 4.6×150 mm, column temperature; 40° C., mobile phase; a sodium 1-undecanesulfonate mixture (water/acetonitrile/acetic acid (100) (54:45:1, v/v/v)) solution (13→10000), flow rate; 1.0 mL/min., detection; 295 nm)

(2) Solution Stability at 5° C.

Pharmaceutical composition 1 for external use was preserved at 5° C. for 4 weeks and observed with the naked eye and under a microscope. The deposition of crystals was not observed.

Example 2

According to the following formulation, Pharmaceutical composition 2 for external use, which is the pharmaceutical composition for external use of the present invention, was prepared in the same way as in Example 1. The composition was preserved at 20° C. for 12 hours and observed with the naked eye or under a microscope. The deposition of crystals was not observed and the composition was in a clear liquid state.

TABLE 2

| Component | % by mass |
|---|---|
| A | |
| Luliconazole | 5 |
| Benzyl alcohol | 1 |
| Ethanol | 4 |
| B | |
| Benzyl alcohol | 1 |
| Lactic acid | 4 |
| Ethanol | 50 |
| C | |
| Isostearyl alcohol | 20 |
| Polyoxyethylene (4.2) lauryl ether | 5 |
| D | |
| Propylene glycol | 10 |
| Total | 100 |

<Characteristics of Pharmaceutical Composition 2 for External Use>

(1) Stability at 60° C.

Pharmaceutical composition 2 for external use was preserved at 60° C. for 3 weeks, and the content of luliconazole and the content of its stereoisomer were measured by an HPLC method described in Example 1. The quantitative value of luliconazole was 99%, and the SE form content and the Z form content were 0.41% by mass and 0.05% by mass, respectively. The values are substantially equal to the values determined immediately after manufacture (quantitative value; 100% by mass, SE form; 0.38% by mass, Z form; 0.01% by mass).

(2) Solution Stability at 5° C.

Pharmaceutical composition 2 for external use was preserved at 5° C. for 2 weeks and observed with the naked eye and under a microscope. The deposition of crystals was not observed. In the preservation for 3 weeks, deposition of crystals was observed with the naked eye and under a microscope.

Example 3

According to the following formulation, Pharmaceutical composition 3 for external use, which is the pharmaceutical composition for external use of the present invention, was prepared in the same way as in Example 1. The composition was preserved at 20° C. for 12 hours and observed with the naked eye or under a microscope. The deposition of crystals was not observed and the composition was in a clear liquid state.

TABLE 3

| Component | % by mass |
|---|---|
| A | |
| Luliconazole | 5 |
| Benzyl alcohol | 1 |
| Ethanol | 4 |
| B | |
| Benzyl alcohol | 1 |
| Lactic acid | 4 |
| Ethanol | 71 |
| C | |
| Diisopropyl adipate | 12 |
| Polyoxyethylene (20) cetyl ether | 2 |
| Total | 100 |

<Characteristics of Pharmaceutical Composition 3 for External Use>

(1) Stability at 60° C.

Pharmaceutical composition 3 for external use was preserved at 60° C. for 3 weeks, and the content of luliconazole and the content of its stereoisomer were measured by the HPLC method described in Example 1. The quantitative value of luliconazole was 99%, and the SE form content and the Z form content were 0.42% by mass and 0.08% by mass, respectively. The values are substantially equal to the values determined immediately after manufacture (quantitative value; 100% by mass, SE form; 0.37% by mass, Z form; 0.01% by mass).

(2) Solution Stability at 5° C.

Pharmaceutical composition 3 for external use was preserved at 5° C. for 4 weeks and observed with the naked eye and under a microscope. The deposition of crystals was not observed.

Example 4

According to the following formulation, Pharmaceutical composition 4 for external use, which is the pharmaceutical composition for external use of the present invention, was prepared in the same way as in Example 1. The composition was preserved at 20° C. for 12 hours and observed with the naked eye or under a microscope. The deposition of crystals was not observed and the composition was in a clear liquid state.

TABLE 4

| Component | % by mass |
|---|---|
| A | |
| Luliconazole | 5 |
| Benzyl alcohol | 1 |
| Ethanol | 4 |
| B | |
| Benzyl alcohol | 1 |
| Lactic acid | 4 |
| Ethanol | 68 |
| C | |
| Diisopropyl adipate | 12 |
| Polyoxyethylene (4.2) lauryl ether | 5 |
| Total | 100 |

<Characteristics of Pharmaceutical Composition 4 for External Use>

(1) Stability at 60° C.

Pharmaceutical composition 4 for external use was preserved at 60° C. for 3 weeks, and the content of luliconazole and the content of its stereoisomer were measured by the HPLC method described in Example 1. The quantitative value of luliconazole was 99.3%, and the SE form content and the Z form content were 0.39% by mass and 0.05% by mass, respectively. The values are substantially equal to the values determined immediately after manufacture (quantitative value; 100% by mass, SE form; 0.4% by mass, Z form; 0.02% by mass).

(2) Solution Stability at 5° C.

Pharmaceutical composition 4 for external use was preserved at 5° C. for 4 weeks and observed with the naked eye and under a microscope. The deposition of crystals was not observed.

Reference Example 3

According to the following formulation, Pharmaceutical composition for external use of the Reference Example 3, was prepared in the same way as in Example 1. The composition was preserved at 20° C. for 12 hours and observed with the naked eye or under a microscope. The deposition of crystals was not observed and the composition was in a clear liquid state. However, when the composition of Reference Example 3 immediately after preparation was applied to a nail, deposition of fine crystals was observed. From these results, it can be understood that a form comprising a diester of a dibasic acid and/or a higher alcohol is preferable.

TABLE 5

| Component | % by mass |
|---|---|
| A | |
| Luliconazole | 5 |
| Benzyl alcohol | 1 |
| Ethanol | 4 |
| B | |
| Benzyl alcohol | 1 |
| Lactic acid | 4 |
| Ethanol | 68 |
| C | |
| Polyoxyethylene (4.2) lauryl ether | 5 |
| Ethanol | 12 |
| Total | 100 |

Example 5

According to the following formulation, Pharmaceutical composition 5 for external use, which is the pharmaceutical composition for external use of the present invention, was prepared in the same way as in Example 1. The composition was preserved at 20° C. for 12 hours and observed with the naked eye or under a microscope. The deposition of crystals was not observed and the composition was in a clear liquid state. Further, the deposition of crystals was not observed after the preservation at 5° C. for 4 weeks and when the composition was applied to a nail.

TABLE 6

| Component | % by mass |
|---|---|
| A | |
| Luliconazole | 6 |
| Benzyl alcohol | 1 |
| Ethanol | 3 |
| B | |
| Benzyl alcohol | 1 |
| Lactic acid | 4 |
| Ethanol | 25 |
| Propylene carbonate | 5 |
| C | |
| Isostearyl alcohol | 20 |
| Polyoxyethylene (4.2) lauryl ether | 5 |
| D | |
| Propylene glycol | 10 |
| Polyethylene glycol 400 | 20 |
| Total | 100 |

<Characteristics of Pharmaceutical Composition 5 for External Use>

(1) Stability at 60° C.

Pharmaceutical composition 5 for external use was preserved at 60° C. for 3 weeks, and the content of luliconazole and the content of its stereoisomer were measured by the HPLC method described in Example 1. The quantitative value of luliconazole was 98.8%, and the SE form content and the Z form content were 0.45% by mass and 0.08% by mass, respectively. The values are substantially equal to the values determined immediately after manufacture (quantitative value; 100% by mass, SE form; 0.4% by mass, Z form; 0.01% by mass).

(2) Solution Stability at 5° C.

Pharmaceutical composition 5 for external use was preserved at 5° C. for 4 weeks and observed with the naked eye and under a microscope. The deposition of crystals was not observed.

INDUSTRIAL APPLICABILITY

The present invention can be applied to a pharmaceutical composition for external use.

What is claimed is:

1. A pharmaceutical composition for external use, comprising:

1) luliconazole of the following general formula (1) and/or a salt thereof;

2) at least one kind selected from a higher alcohol which is in a liquid state at 1 atm and 25° C. and a diester of a dibasic acid, provided that a diester carbonate is excluded; and 3) 5 to 20% by mass with respect to a total amount of the pharmaceutical composition of at least one polyoxethylene alkyl ether selected from polyoxyethylene lauryl ether and polyoxyethylene cetyl ether;

General formula (1)

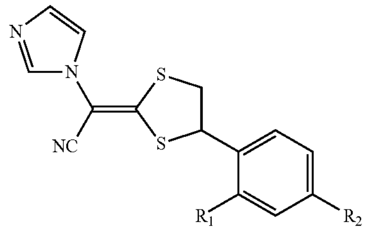

wherein $R_1$ and $R_2$ represents a chlorine atom.

2. The pharmaceutical composition for external use according to claim 1, wherein:

the higher alcohol which is in a liquid state at 1 atm and 25° C. is isostearyl alcohol and/or the diester of a dibasic acid is diisopropyl adipate.

3. The pharmaceutical composition for external use according to claim 1, which has the following properties:

1) when the compound represented by the general formula (1) and/or a salt thereof has a stereoisomer, an amount of the stereoisomer of the compound and/or a salt thereof produced under a preservation condition of 60° C. for 3 weeks is 1% by mass or less with respect to a total mass of the compound and/or a salt thereof at the beginning of preservation;

2) the composition is in a clear liquid state when preserved at a constant temperature of 20° C. immediately after manufacture; and 3) no crystal is deposited when the composition is preserved at 5° C. for 2 weeks after manufacture.

4. The pharmaceutical composition for external use according to claim 1, further comprising at least one kind of solvent selected from crotamiton and N-methyl-2-pyrrolidone.

5. A method for treatment of tinea unguium comprising administering the pharmaceutical composition of claim 1 in an effective amount to an individual in need thereof.

6. The method according to claim 5, wherein the pharmaceutical composition for external use comprises:

(a) isostearyl alcohol and/or diisopropyl adipate, and (b) polyoxyethylene lauryl ether and/or polyoxyethylene cetyl ether.

7. The method according to claim 5, wherein the pharmaceutical composition for external use further comprises at least one kind of solvent selected from crotamiton and N-methyl-2-pyrrolidone.

* * * * *